United States Patent [19]

Scher et al.

[11] Patent Number: 5,912,207

[45] Date of Patent: Jun. 15, 1999

[54] STABLE HERBICIDAL COMPOSITIONS CONTAINING METAL CHELATES OF HERBICIDAL DIONE COMPOUNDS

[75] Inventors: Herbert B. Scher, Moraga; Jinling Chen, El Cerrito, both of Calif.

[73] Assignee: Zeneca Limited, United Kingdom

[21] Appl. No.: 08/792,340

[22] Filed: Jan. 31, 1997

[51] Int. Cl.⁶ ............................. A01N 55/02; C07F 19/00
[52] U.S. Cl. ..................... 504/190; 504/191; 504/348; 544/64; 544/225; 546/2; 546/11; 548/402
[58] Field of Search ..................... 504/116, 190, 504/348; 544/64, 225; 546/2, 11; 548/402

[56] References Cited

U.S. PATENT DOCUMENTS

| | | | |
|---|---|---|---|
| 4,507,142 | 3/1985 | Pace et al. | 71/83 |
| 4,780,127 | 10/1988 | Michaely et al. | 71/103 |
| 4,938,796 | 7/1990 | Buren et al. | 71/98 |
| 5,006,158 | 4/1991 | Carter | 71/98 |
| 5,006,162 | 4/1991 | Carter | 71/123 |
| 5,089,046 | 2/1992 | Lee et al. | 71/103 |
| 5,092,919 | 3/1992 | Nguyen | 71/122 |

FOREIGN PATENT DOCUMENTS 0 496 630   7/1992   European Pat. Off. .
0 496 631   7/1992   European Pat. Off. .

*Primary Examiner*—S. Mark Clardy
*Attorney, Agent, or Firm*—David P. LeCroy

[57] ABSTRACT

Metal chelates of herbicidal dione compounds of the formula

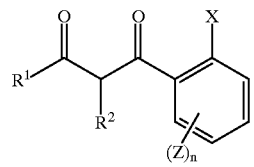

are chemically stable for long periods of time under normal as well as extreme temperature conditions. Chemically stable liquid herbicidal formulations containing metal chelates of the herbicidal compounds of formula (I) and water, an organic solvent or a liquid co-herbicide and processes for producing chemically stable herbicidal compositions containing such metal chelates are also described.

24 Claims, No Drawings

STABLE HERBICIDAL COMPOSITIONS CONTAINING METAL CHELATES OF HERBICIDAL DIONE COMPOUNDS

FIELD OF THE INVENTION

The present invention relates to chemically stable metal chelates of herbicidal dione compounds. According to one aspect of the invention, these chemically stable metal chelates of herbicidal dione compounds can be used in liquid formulations or with a liquid carrier, optionally with another agriculturally active chemical.

BACKGROUND OF THE INVENTION

Herbicidally active compounds are used to control or modify the growth of plants. Herbicidal compositions containing one or more active herbicidal compounds can be formulated and applied in a variety of ways. The object of a particular formulation is to apply the herbicidal compound(s) to an area where plant growth control is desired in a convenient, safe and effective way.

The choice of formulation and mode of application for any given herbicidal compound may affect its activity, and selection must be made accordingly. Herbicidal compositions may thus be formulated as granules, as wettable powders, as emulsifiable concentrates, as powders or dusts, as flowables, as solutions, as suspensions or emulsions, or as controlled release forms such as microcapsules.

Wettable powders are in the form of finely divided particles which disperse readily in water or other liquid carriers. The particles contain the active ingredient retained in a solid matrix or the active ingredient can be commingled with the solid matrix particles. Typical solid matrices include fuller's earth, kaolin clays, silicas and other readily wet organic or inorganic solids. Wettable powders normally contain about 5% to about 95% of the active ingredient plus a small amount of wetting, dispersing, or emulsifying agent.

Emulsifiable concentrates are homogeneous liquid compositions dispersible in water or other liquid, and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally are applied as a spray to the area to be treated. The amount of active ingredient may range from about 0.5% to about 95% of the concentrate.

Granular formulations include both extrudates and relatively coarse particles, and are usually applied without dilution to the area in which suppression of vegetation is desired. Typical carriers for granular formulations include sand, fuller's earth, attapulgite clay, bentonite clays, montmorillonite clay, vermiculite, perlite and other organic or inorganic materials which absorb or which can be coated with the active compound. Granular formulations normally contain about 5% to about 25% active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules and encapsulated granules are typical controlled release formulations. Microcapsules are typically droplets of the active material enclosed in an inert porous shell which allows escape of the enclosed material to the surroundings at controlled rates. Encapsulated droplets are typically about 1 to 50 microns in diameter. The enclosed liquid typically constitutes about 50 to 95% of the weight of the capsule, and may include solvent in addition to the active compound. Encapsulated granules are generally porous granules with porous membranes sealing the granule pore openings, retaining the active species in liquid form inside the granule pores. Granules typically range from 1 millimeter to 1 centimeter, preferably 1 to 2 millimeters in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrenebutadiene copolymers, polyacrylonitriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as acetone, alkylated naphthalenes, xylene and other organic solvents. Pressurized sprayers, wherein the active ingredient is dispersed in a finely-divided form as a result of atomization and vaporization of a low boiling dispersant solvent carrier, may also be used.

Although dusts and granular formulations are used for the application of some herbicidal compounds, drift due to wind is a problem with such dry formulations and, consequently, liquid formulations are preferred. Liquid formulations are also advantageous in that they permit the "tank mixing" of two or more agriculturally active formulations at the grower site.

The discovery of herbicidal dione compounds having the general formula (I):

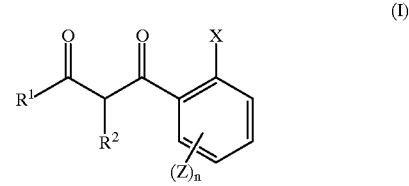

wherein $R^1$, $R^2$, X and Z have the meanings set forth hereinafter, has resulted in considerable field testing of these compounds alone and in combination with other agriculturally active compounds for various uses worldwide.

These herbicidal dione compounds have the disadvantage that in water and other solvents (in which there is appreciable solubility) they can undergo decomposition. This decomposition occurs at such a rate that the use of these herbicidal dione compounds in aqueous herbicidal formulations or formulations containing an organic solvent or liquid co-herbicide is impractical, unless the formulation is prepared immediately or within a short period of time prior to use.

It is, therefore, an object of this invention to provide metal chelates of the herbicidal dione compounds of formula (I) which are chemically stable for long periods of time under normal as well as extreme temperature conditions. Another object of the present invention is to provide liquid herbicidal formulations based on the herbicidal dione compounds of formula (I) and water, an organic solvent or a liquid co-herbicide, which formulations are chemically stable.

SUMMARY OF THE INVENTION

The present invention relates to chemically stable metal chelates of herbicidal dione compounds of the formula (I):

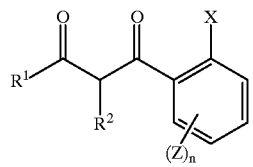

wherein $R^1$ represents a straight- or branched-chain alkyl, alkenyl or alkynyl group containing up to six carbon atoms which is optionally substituted by one or more halogen atoms; a cycloalkyl group containing from three to six carbon atoms optionally substituted by one or more $R^3$ groups or one or more groups selected from halogen, $-CO_2R^4$; $-SR^5$ and $-OR^5$; a cycloalkenyl group containing five or six carbon atoms optionally substituted by one or more $R^3$ groups or one or more halogen atoms or a group $-CO_2R^4$ or a group of the formula $-(CH_2)_p$-phenyl-$(R^6)_q$;

$R^2$ represents cyano; $-COR^7$; $-CO_2R^7$; or $-S(O)_mR^8$; or $R^1$ and $R^2$ together with the carbon atoms to which they are attached form a five- or six-membered 1,3-cycloalkanedione group, which 1,3-cycloalkanedione group is optionally substituted with from one to six substituents independently selected from halogen, $(C_1-C_6)$alkyl, $(C_1-C_6)$alkoxy, $(C_1-C_6)$haloalkyl, $(C_3-C_6)$cycloalkyl, cyano, nitro, $(C_1-C_6)$haloalkoxy, $-CO_2R^9$, $-S(O)_mR^{10}$, $-NR^{11}R^{12}$, $-C(O)R^{13}$, $-SO_2NR^{11}R^{12}$, phenyl and phenyl substituted with one or more halo or $C_1-C_4$ alkyl groups, wherein two substituents on the same carbon atom of the 1,3-cycloalkanedione group taken together can form an alkylene group having 2 to 6 carbon atoms;

$R^3$ represents a straight- or branched chain alkyl, alkenyl or alkynyl group containing up to six carbon atoms optionally substituted by one or more halogen atoms; or a cycloalkyl group containing from three to six carbon atoms.

$R^4$ represents a straight- or branched-chain alkyl group containing up to six carbon atoms optionally substituted by one or more halogen atoms; or a cycloalkyl group containing from three to six carbon atoms;

$R^5$ represents a straight- or branched-chain alkyl group containing up to three carbon atoms.

$R^6$ represents a halogen atom or a group selected from $-R^4$, nitro, cyano, $-CO_2R^4$, $-NR^{61}R^{62}$ and $-OR^4$;

$R^{61}$ represents hydrogen, a straight- or branched-chain alkyl group containing up to six carbon atoms optionally substituted by one or more halogen atoms, or a cycloalkyl group containing from three to six carbon atoms;

$R^{62}$ represents a straight- or branched-chain alkyl group containing up to six carbon atoms optionally substituted by one or more halogen atoms, a cycloalkyl group containing from three to six carbon atoms, or a group selected from $-COR^4$, $-CO_2R^4$ and $-CONR^4R^{61}$; wherein $R^4$ and $R^{61}$ are part of a group $-CONR^4R^{61}$ they may, together with the nitrogen to which they are attached, form a five- or six-membered ring optionally having one additional heteroatom in the ring which is oxygen or nitrogen (e.g., pyrrolidine, morpholine, pyrrole, piperidine and piperazine), wherein the ring is optionally substituted by one or more alkyl groups containing up to three carbon atoms; and when $R^{61}$ and $R^{62}$ are part of a group $-NR^{61}R^{62}$ they may, together with the nitrogen to which they are attached, form a five- or six-membered ring optionally having one additional heteroatom in the ring which is oxygen or nitrogen (e.g., pyrrolidine, morpholine, pyrrole, piperidine and piperazine), wherein the ring is optionally substituted by one or more alkyl groups containing up to three carbon atoms;

$R^7$ represents hydrogen or straight- or branched-chain alkyl group containing up to six carbon atoms;

$R^8$ represents $(C_1-C_6)$alkyl, $(C_1-C_6)$haloalkyl, $(C_1-C_6)$cyanoalkyl $(C_3-C_8)$cycloalkyl optionally substituted with halogen, cyano or $(C_1-C_4)$alkyl; or phenyl optionally substituted with one to three of the same or different halogen, nitro, cyano, $(C_1-C_4)$haloalkyl, $(C_1-C_4$ alkyl, $(C_1-C_4)$ alkoxy or $-S(O)_mR^8$;

$R^9$ represents $(C_1-C_4)$alkyl;

$R^{10}$ represents $(C_1-C_4)$alkyl, $(C_1-C_4)$alkyl substituted with halogen or cyano, phenyl or benzyl;

$R^{11}$ and $R^{12}$ independently represents hydrogen or $(C_1-C_4)$alkoxy;

$R^{13}$ represents $(C_1-C_4)$alkyl or $(C_1-C_4)$alkoxy;

X represents a halogen atom; a straight- or branched-chain alkyl or alkoxy group containing up to six carbon atoms which is optionally substituted by one or more groups $-OR^{15}$ or one or more halogen atoms; or a group selected from nitro, cyano, $-CO_2R^{16}$, $-S(O)_mR^{15}$, $-O(CH_2)_rOR^{15}$, $-COR^{16}$, $-OSO_2R^{18}$, $-NR^{16}R^{17}$, $-SO_2NR^{16}R^{17}$, $-CONR^{16}R^{17}$ and $-CSNR^{16}R^{17}$;

$R^{15}$ represents a straight- or branched-chain alkyl group containing up to six carbon atoms which is optionally substituted by one or more halogen atoms;

$R^{16}$ and $R^{17}$ each independently represents a hydrogen atom; or a straight- or branched-chain alkyl group containing up to six carbon atoms which is optionally substituted by one or more halogen atoms;

$R^{18}$ represents a straight- or branched-chain alkyl, alkenyl or alkynyl group containing up to six carbon atoms optionally substituted by one or more halogen atoms; or a cycloalkyl group containing from three to six carbon atoms;

each Z independently represents halo, nitro, cyano, $S(O)_mR^2$, $OS(O)_mR^2$, $(C_1-C_6)$alkyl, $(C_1-C_6)$alkoxy, $(C_1-C_6)$haloalkyl, $(C_1-C_6)$haloalkoxy, carboxy, $(C_1-C_6)$alkylcarbonyloxy, $(C_1-C_6)$alkoxycarbonyl, $(C_1-C_6)$alkylcarbonyl, amino, $(C_1-C_6)$alkylamino, $(C_1-C_6)$dialkylamino having independently the stated number of carbon atoms in each alkyl group, $(C_1-C_6)$alkylcarbonylamino, $(C_1-C_6)$alkoxycarbonylamino, $(C_1-C_6)$alkylaminocarbonylamino, $(C_1-C_6)$dialkylaminocarbonylamino having independently the stated number of carbon atoms in each alkyl group, $(C_1-C_6)$alkoxycarbonyloxy, $(C_1-C_6)$alkylaminocarbonyloxy, $(C_1-C_6)$dialkylaminocarbonyloxy, phenylcarbonyl, substituted phenylcarbonyl, phenylcarbonyloxy, substituted phenylcarbonyloxy, phenylcarbonylamino, substituted phenylcarbonylamino, phenoxy or substituted phenoxy;

m is zero, one or two;

n is zero or an integer from one to four;

p is zero or one;

q is zero or an integer from one to five; and r is one, two or three.

As used herein, the terms "halogen" and "halo" include fluorine, chlorine, bromine and iodine atoms. In polyhalogenated groups, the halogens may be the same or different. The term "substituted" in the terms "substituted phenylcarbonyl," "substituted phenylcarbonyloxy," "substituted phenylcarbonylamino" and "substituted phenoxy" means having one to five substituents, which may be the same or different, selected from the following: halo, nitro, cyano, $S(O)_mR^2$, $(C_1-C_6)$alkyl, $(C_1-C_6)$alkoxy, $(C_1-C_6)$haloalkyl, $(C_1-C_6)$haloalkoxy, carboxy, $(C_1-C_6)$alkylcarbonyloxy, $(C_1-C_6)$alkylcarbonyl, $(C_1-C_6)$alkoxycarbonyl, $(C_1-C_6)$alkylcarbonylamino, amino, $(C_1-C_6)$alkylamino and $(C_1-C_6)$dialkylamino having independently the stated number of carbon atoms in each group.

DETAILED DESCRIPTION OF THE INVENTION

Many herbicidal dione compounds of formula (I) have been described in a number of U.S. and foreign patent publications in recent years. Two known groups of compounds within the scope of formula (I) are particularly useful in the present invention. These two groups of compounds are:

(A) 2-(substituted benzoyl)-1,3-cyclohexanedione compounds of the formula:

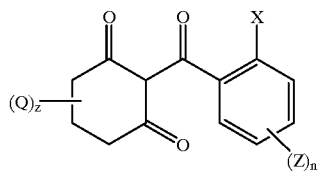

(II)

wherein X, Z and n have the meanings given above; each Q independently represents $C_1-C_4$ alkyl or $-CO_2R^a$ wherein $R^a$ is $C_1-C_4$ alkyl; and z is 0 or an integer from 1 to 6; and
(B) 2-cyano-1,3-dione compounds of the formula:

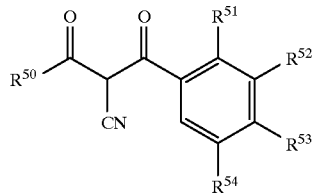

(III)

wherein:

$R^{50}$ is a straight- or branched-chain alkyl group containing up to six carbon atoms which is optionally substituted by one or more halogen atoms which may be the same or different; or a cycloalkyl group containing from three to six carbon atoms which is optionally substituted by one or more groups selected from $R^{55}$ and one or more halogen atoms which may be the same or different;

one of $R^{51}$ and $R^{53}$ is $-S(O)_tR^{56}$ and the other of $R^{51}$ and $R^{53}$ is a halogen atom; a straight- or branched-chain alkyl group containing up to six carbon atoms which is substituted by $-OR^{55}$; $-R^{55}$; nitro; cyano; $-SR^{55}$; $-OR^{55}$; $-O(CH_2)_sOR^{55}$; or $-CO_2R^{55}$; and when $R^{51}$ is $-S(O)_tR^{56}$, $R^{53}$ may be hydrogen;

$R^{52}$ and $R^{54}$, which may be the same or different, each is a halogen atom; a hydrogen atom; a straight- or branched-chain alkyl group containing up to six carbon atoms which is substituted by $-OR^{55}$; $-R^{55}$; nitro; cyano; $-OR^{55}$; $-O(CH_2)_sOR^{55}$; or $-CO_2R^{55}$;

$R^{55}$ and $R^{56}$, which may be the same or different, each is a straight- or branched-chain alkyl group containing up to six carbon atoms which is optionally substituted by one or more halogen atoms which may be the same or different;

s is an integer from 1 to 3; and t is zero, 1 or 2.

2-(substituted benzoyl)-1,3-cyclohexanedione compounds of formula II are described, inter alia, in U.S. Pat. Nos. 4,780,127, 4,938,796, 5,006,158 and 5,089,046, the disclosures of which are incorporated herein by reference. Herbicidal 2-(substituted benzoyl)-1,3-cyclohexanedione compounds for use in this invention may be prepared by the methods described in the aforementioned patent publications, or by the application and adaptation of known methods used or described in the chemical literature.

Especially preferred 2-(substituted benzoyl)-1,3-cyclohexanedione compounds useful in the present invention include those in which z is zero; X is chloro, bromo, nitro, cyano, $C_1-C_4$ alkyl, $-CF_3$, $-S(O)_mR^{15}$ or $-OR^{15}$; n is one or two; and each Z is independently chloro, bromo, nitro, cyano, $C_1-C_4$ alkyl, $-CF_3$, $-OR^{15}$, $-OS(O)_mR^2$ or $-S(O)_mR^2$. Examples of preferred cyclohexanedione compounds are 2-(2'-nitro-4'-methylsulfonylbenzoyl)-1,3-cyclohexane-dione, 2-(2'-nitro-4'-methylsulfonyloxybenzoyl)-1,3-cyclohexanedione and 2-(2'-chloro-4'-methylsulfonylbenzoyl)-1,3-cyclohexanedione.

Compounds of formula (II) may exist in enolic tautomeric forms that may give rise to geometric isomers. Furthermore, in certain cases, the various substituents may contribute to optical isomerism and/or stereoisomerism. All such forms are embraced within compounds useful in the present invention.

2-Cyano-1,3-dione herbicide compounds useful in the present invention are described in European Patent Publication Nos. 0 496 630 and 0 496 631, the disclosures of which are incorporated herein by reference thereto. Herbicidal 2-cyano-1,3-dione compounds for use in this invention may be prepared by the methods described in the aforementioned patent publications, or by the application and adaptation of known methods used or described in the chemical literature. Preferred 2-cyano-1,3-diones of formula (III) for use in the present invention are those in which $R^{50}$ is a cycloalkyl group, most preferably a cyclopropyl group. Examples of preferred compounds of formula (III) are: 2-cyano-1-[2-chloro-3-ethoxy-4-(ethylsulfonyl)phenyl]-3-cyclopropylpropan-1,3-dione; 2-cyano-1-[4-chloro-2-(methylsulfonyl)phenyl]-3-cyclopropylpropan-1,3-dione; 2-cyano-1-[2-methylsulfonyl-4-(trifluoromethyl)phenyl]-3-cyclopropylpropan-1,3-dione; and 2-cyano-1-[4-bromo-2-(methylsulfonyl)phenyl]-3-cyclopropylpropan-1,3-dione.

Compounds of formula (III) may exist in enolic tautomeric forms that may give rise to geometric isomers around the enolic double bond. Furthermore, in certain cases, the substituents $R^{50}$, $R^{51}$, $R^{52}$, $R^{53}$, $R^{54}$, $R^{55}$ and $R^{56}$ may contribute to optical isomerism and/or stereoisomerism. All such forms are embraced within 2-cyano-1,3-dione compounds useful in the present invention.

The herbicidal dione compounds useful in the present invention have been described above. The metal chelates of the herbicidal compounds of formula (I) can be formed by adding the desired metal ion to the dione compound in the presence of water or an organic solvent or carrier. Conveniently, an aqueous solution of an appropriate metal salt is added to a liquid medium, such as water or an organic solvent, having the herbicidal dione compound dispersed or dissolved therein, and then the metal salt and the dione compound are allowed to react at room temperature for a period of time sufficient to convert all of the dione compound to its corresponding metal chelate compound. Following conversion of the dione to its corresponding metal chelate, the pH of the mixture is adjusted to be between about 2 and about 7, using an acid such as hydrochloric acid, nitric acid, sulfuric acid or the like.

The formation of the metal chelate compound can be accomplished in an aqueous phase of a composition containing another agriculturally active compound, such as a herbicide. According to one process, the dione compound is milled and then added to the aqueous phase of an herbicidal composition having a microencapsulated agriculturally active ingredient suspended in the aqueous phase. An aqueous solution of an appropriate metal salt is then added to the mixture of the herbicidal composition and the dione compound, and allowed to react at room temperature for a period of time sufficient to convert all of the dione compound to its corresponding metal chelate. Again, the pH of the resulting mixture is adjusted to be between about 2 and about 7, using an appropriate acid.

According to another process of the present invention, the dione compound need not be milled prior to formation of the metal chelate. In this process, the dione compound is added to the aqueous phase of an herbicidal composition having a microencapsulated agriculturally active ingredient suspended therein. The pH of the resultant mixture is then adjusted to about 10, using sodium hydroxide or another base. An aqueous solution of an appropriate metal salt is then added to the mixture with stirring and crystals of the metal chelate of the dione compound form instantly. The reaction is allowed to proceed until all of the dione compound is converted to its corresponding metal chelate. Finally, the pH of the mixture is adjusted to between about 2 and about 7 using an acid, such as hydrochloric acid.

According to another aspect of the invention, stable solid herbicidal compositions containing metal chelates of dione compounds can also be produced. These solid compositions are formed by preparing an aqueous formulation of a metal chelate of a dione compound alone or in the presence of a another herbicide, as described above, and then spray drying the resultant metal chelate composition to produce a stable, dry particulate formulation which can be added to water or another carrier for application to an area for control of undesired vegetation.

Metal ions which may be useful in forming the metal chelate compounds of the present invention include di- and trivalent transition metal ions such as $Cu^{+2}$, $Zn^{+2}$, $Co^{+2}$, $Fe^{+2}$, $Ni^{+2}$, and $Fe^{+3}$. The selection of a particular metal ion to form the metal chelate compound will depend upon the dione compound to be chelated. Certain metal ions may be more effective in imparting physical and/or chemical stability to a specific dione compound within the scope of formula (I) than others. Those skilled in the art will be able to readily determine the appropriate metal ion for use with a specific dione compound, without undue experimentation. The preferred metal ions are divalent transition metal ions, particularly $Cu^{+2}$, $Zn^{+2}$ and $Co^{+2}$, with $Cu^{+2}$ being especially preferred.

Any appropriate salt which would be a source of a di- or trivalent metal ion may be used to form the metal chelate of the dione compound in accordance with this invention. Particularly suitable salts include: chlorides, sulfates, nitrates, carbonates, phosphates and acetates.

It has been found that the stability of the herbicidal metal chelate compositions of the present invention is pH dependent. The pH of the metal chelate compositions should be between about 2 and about 7, with an acidic pH of less than about 6 being preferred for most metals. Generally, it is believed that for $Cu^{+2}$ chelate compositions the pH should be between about 4 and 6; for $Co^{+2}$ between about 3 and 5; and for $Ni^{+2}$ and $Zn^{+2}$ about 5. The optimum pH for a particular metal chelate composition can be determined using routine experimental techniques.

It has also been found that an excess of metal ion in the final formulation can increase the chemical stability of the dione compound. For divalent metals, the stoichiometric molar ratio of dione compound to metal ion is 2:1. Thus, the minimum amount of metal ion to be added to the dione compound to produce the metal chelate is an amount sufficient to provide a molar ratio of dione to metal ion of 2:1. However, amounts in excess of the stoichiometric amount may enhance the chemical stability of the dione compound, and a molar ratio of dione to metal ion of between 2:1 and 2:5 is preferred, with a molar ratio of between about 2:1 and 2:2 being especially preferred.

The metal chelates of the dione compounds are chemically stable in solid or dry form by themselves, but it is their chemical stability in the presence of water or another liquid medium or a co-herbicide which makes these chelates particularly useful in herbicidal formulations. As compared to the unchelated dione compounds, the metal chelates exhibit enhanced chemical stability in any liquid medium in which the parent dione compound is at least partially soluble. The metal chelates of the dione compounds of formula (I) are chemically stable in water, in other polar solvents such as dibutyl phthalate, in commonly used agriculturally acceptable solvents and carriers such as SOLVESSO 200, and in liquid agriculturally active ingredients such as acetochlor and other acetanilides, thiafluamide, butroxydim, esters of bromoxynil, MCPA, and 2,4-D, and the like.

Liquid formulations containing the chemically stable metal chelates of the herbicidal dione compounds of formula (I) can be applied directly to an area where control of undesired vegetation is located, using known techniques for applying liquid or flowable herbicide formulations. The stable, liquid formulations containing an herbicidal metal chelate according to the invention can also be diluted to a desired concentration of active ingredient(s) prior to application, or can be tank-mixed with one or more additional herbicidal or other agricultural compositions. Specific examples of other herbicides which may be incorporated in an herbicidal formulation with the metal chelates according to the invention include acetanilides, tralkoxydim, bromoxynil and its esters, thiafluamide, MCPA and its esters, 2,4-D and its esters, and fluroxypyr meptyl.

The following examples are for illustrative purposes only and are not intended as necessarily representative of the overall testing performed and are not intended to limit the invention in any way.

EXAMPLE 1

This is an example of one process for producing an herbicidal composition containing a copper chelate of a 2-(substituted benzoyl)-1,3-cyclohexanedione herbicide.

Particulate, air milled technical grade 2-(2'-nitro-4'-methylsulfonylbenzoyl)-1,3-cyclohexanedione ("NMSBC") was blended with an herbicidal formulation containing microencapsulated acetochlor suspended in a continuous aqueous phase at an acetochlor to NMSBC weight ratio of 10:1. An aqueous solution of cupric chloride was then added to the formulation in a molar ratio of NMSCB to copper to 2:1. The resultant mixture was allowed to react overnight at room temperature to produce the copper chelate of NMSBC in the aqueous phase of the formulation. The pH of the final formulation was then adjusted to 3 using hydrochloric acid.

The same process was then employed to produce a formulation in which the molar ratio of NMSBC to copper was 2:5.

The process described above was then employed to produce two formulations in which the molar ratio of NMSBC to copper was 1:2 and 2:5, respectively, and the pH of the final formulations was adjusted to 5.0 using hydrochloric acid.

Samples of each of these formulations were stored at 50° C. for four weeks to determine their chemical stability. After storage, samples were extracted and analyzed by high pressure liquid chromatography (HPLC). The procedure for extracting NMSBC from the copper chelate for analysis was as follows. To convert the copper chelate of NMSBC to its parent compound, the formulation was treated with concentrated hydrochloric acid. Concentrated hydrochloric acid (5 grams) was added to a 1 gram sample of the formulation. The mixture was sonicated for 5 minutes. Then, 10 grams of chloroform was added to extract NMSBC. After centrifuging to get phase separation, 5 grams of the chloroform phase was withdrawn. The chloroform was allowed to evaporate and the remaining NMSBC was analyzed by HPLC. The results of these storage stability tests are shown in Table 1 below. The results of the same chemical stability testing conducted on control sample formulations in which NMSBC was suspended in the aqueous phase of a microencapsulated acetochlor formulation without chelating the NMSBC are also shown in Table 1.

TABLE 1

| Molar ratio of NMSBC: $Cu^{+2}$ | pH | Storage Temperature | Weight % of NMSBC remaining after 4 week storage |
|---|---|---|---|
| 2:1 | 3.0 | 50° C. | 97% |
| 2:5 | 3.0 | 50° C. | 97% |
| 2:1 | 5.0 | 50° C. | 97.5% |
| 2:5 | 5.0 | 50° C. | 100% |
| No $Cu^{+2}$ | 3.0 | 50° C. | 65% |
| No $Cu^{+2}$ | 5.0 | 50° C. | 30% |

The above results clearly demonstrate the superior chemical stability of the copper chelate of NMSBC as compared to non-chelated NMSBC under the same conditions.

EXAMPLE 2

The chemical stability of various metal chelates dispersed in water was studied. Using appropriate metal salt solutions, the following metal chelates of NMSBC were prepared: $Cu^{+2}$, $Ca^{+2}$, $Zn^{+2}$, $Mg^{+2}$, $Al^{+3}$, $Co^{+2}$, $Fe^{+3}$, $Fe^{+2}$ and $Ni^{+2}$. In each instance, NMSBC was dispersed in water and then the appropriate aqueous solution of a metal salt was added in an amount sufficient to provide a molar excess of metal ion with respect to NMSBC. The resultant mixture was allowed to react overnight at room temperature to permit an aqueous dispersion of the respective metal chelate to form. The pH of each metal chelate suspension was adjusted to about 7 or less using hydrochloric acid. Samples were stored at 50° C. for four weeks and then extracted and analyzed as described in Example 1. Table 2 below shows the results obtained from this four week storage test. Table 2 also shows the results of the same chemical stability testing conducted on a control sample in which NMSBC was not chelated.

TABLE 2

| Metal Ion | Storage pH | Weight % of NMSBC remaining after 4 week storage at 50° C. |
|---|---|---|
| $Al^{+3}$ | 3.0 | 69% |
| $Al^{+3}$ | 5.4 | 70% |

TABLE 2-continued

| Metal Ion | Storage pH | Weight % of NMSBC remaining after 4 week storage at 50° C. |
|---|---|---|
| $Ca^{+2}$ | 5.0 | 66% |
| $Ca^{+2}$ | 7.6 | 24% |
| $Co^{+2}$ | 3.0 | 97% |
| $Co^{+2}$ | 5.0 | 85% |
| $Cu^{+2}$ | 5.0 | 100% |
| $Cu^{+2}$ | 7.0 | 99% |
| $Fe^{+2}$ | 2.0 | 84% |
| $Fe^{+3}$ | 2.0 | 73% |
| $Fe^{+3}$ | 7.0 | 38% |
| $Mg^{+2}$ | 3.2 | 80% |
| $Mg^{+2}$ | 5.4 | 76% |
| $Ni^{+2}$ | 5.0 | 93% |
| $Ni^{+2}$ | 7.0 | 61% |
| $Zn^{+2}$ | 5.0 | 100% |
| None | 5.0 | 81% |

The results shown in Table 2 demonstrate that the divalent transition metal chelates of NMSBC, particularly the $Zn^{+2}$, $Co^{+2}$ and $Ni^{+2}$ chelates, and most especially the $Cu^{+2}$ chelate, exhibit superior chemical stability in water as compared to non-chelated NMSBC.

EXAMPLE 3

The chemical stability of various metal chelates of NMSBC in the aqueous phase of a microencapsulated acetochlor formulation was studied. The procedure of Example 1 was followed, using the appropriate metal salt solutions, to prepare the following metal chelates of NMSBC: $Cu^{+2}$, $Ca^{+2}$, $Zn^{+2}$, $Mg^{+2}$, $Al^{+3}$, $Co^{+2}$, $Fe^{+3}$, $Fe^{+2}$ and $Ni^{+2}$. In each instance, the NMSBC was complexed with the metal ions in the aqueous phase outside the acetochlor microcapsules. The amount of metal ion added to the aqueous phase was an amount sufficient to provide a molar ratio of NMSBC to metal ion of 2:5. Samples were stored at 50° C. for four weeks and then extracted and analyzed as described in Example 1. Table 3 below shows the results obtained from this four week storage test. These results indicate that the chemical stability of NMSBC varies depending upon the metal ion used to form the chelate and varies depending upon the storage pH. Table 3 also shows the result of the same chemical stability testing conducted on a control sample formulation in which NMSBC was suspended in the aqueous phase of a microencapsulated acetochlor formulation without chelating the NMSBC.

TABLE 3

| Metal Ion | Storage pH | Weight % of NMSBC remaining after storage at 50° C. | |
|---|---|---|---|
| | | 2 weeks | 4 weeks |
| $Al^{+}$ | 3.0 | 38.5% | |
| $Al^{+}$ | 4.5 | 34.8% | |
| $Ca^{+2}$ | 5.0 | 6.9% | 2.2% |
| $Ca^{+2}$ | 7.4 | 43.5% | 38.3% |
| $Co^{+2}$ | 3.0 | 83.8% | 77.3% |
| $Co^{+2}$ | 5.0 | 95.7% | 91.8% |
| $Cu^{+2}$ | 3.0 | 99.1% | 102.9% |
| $Cu^{+2}$ | 5.0 | 100.2% | 98.9% |
| $Fe^{+2}$ | 2.0 | 49.9% | |
| $Fe^{+3}$ | 1.0 | 64.3% | |
| $Fe^{+3}$ | 2.0 | 54.1% | |
| $Mg^{+2}$ | 5.0 | 19.9% | |

TABLE 3-continued

| Metal Ion | Storage pH | Weight % of NMSBC remaining after storage at 50° C. | |
|---|---|---|---|
| | | 2 weeks | 4 weeks |
| $Ni^{+2}$ | 5.0 | 30.4% | |
| $Zn^{+2}$ | 5.0 | 92.8% | 93.1% |
| None | 3.0 | 75.2% | 64.9% |
| None | 5.0 | 38.2% | 30.0% |

The results shown in Table 3 demonstrate the improved chemical stability of the $Cu^{+2}$, $Co^{+2}$ and $Zn^{+2}$ chelates of NMSBC in an aqueous formulation of acetochlor microcapsules as compared to a non-chelated NMSBC.

EXAMPLE 4

Storage tests at 50° C., as described above, were conducted to determine the effect of storage pH on the chemical stability of several different metal chelates of NMSBC. Chemical stability determinations were made after 2 weeks and 4 weeks of storage. Formulations of metal chelates of NMSBC in the aqueous phase of a suspension of microencapsulated acetochlor were made according to the processes described in Examples 1 and 3, except that the molar ratio of metal ion to NMSBC used in each formulation was 1.1:2. Table 4 below shows the chemical stability of NMSBC complexed with $Cu^{+2}$, $Zn^{+2}$ and $Co^{+2}$ in the aqueous phase of a formulation of microencapsulated acetochlor at various pH levels of the final formulation. These results indicate that the chemical stability of the metal chelates of NMSBC is dependent on the storage pH of the formulation.

TABLE 4

| Metal Ion | Storage pH | Weight % of NMSBC remaining after storage at 50° C. | |
|---|---|---|---|
| | | 2 weeks | 4 weeks |
| $Cu^{+2}$ | 5.0 | 97.0% | 97.5% |
| | 7.0 | 97.7% | 98.8% |
| | 9.0 | 86.2% | 80.8% |
| | 10.0 | 69.6% | |
| $Zn^{+2}$ | 5.0 | 59.5% | |
| | 7.0 | 65.1% | |
| | 9.0 | 23.1% | |
| | 10.0 | 10.5% | |
| $Co^{+2}$ | 5.0 | 68.0% | |
| | 7.0 | 37.3% | |
| | 9.0 | 10.7% | |
| | 10.0 | 4.6% | |

EXAMPLE 5

This example shows the preemergence herbicidal activity of formulations prepared according to Examples 1 and 3, which contain metal chelates of NMSBC together with microencapsulated acetochlor in the aqueous phase the formulation. A control formulation containing NMSBC suspended in the aqueous phase of a microencapsulated acetochlor formulation was also tested, for comparison purposes. The herbicidal testing was conducted as follows.

On the day preceding treatment, seeds of several different weed species were planted in sandy loam soil containing only trace organic matter. Propagules were sown in individual rows using one species per row across the width of an aluminum flat. Seeding depths ranged from 1.0 to 1.5 cm and plant densities ranged from 3 to 25 plants per row depending on individual plant species.

For the screening tests results shown in Table 5, the grass weeds planted were barnyardgrass (*Echinochloa crus-galli*); large crabgrass (*Digitaria sanguinalis*); rigid ryegrass (*Lolium rigidum*); wild proso millet (*Panicum miliaceum*); and shattercane (*Sorghum vulgare*). The average control achieved against these grass species ("AVG") is indicated in Table 5. The broadleaf weeds planted were velvetleaf (*Abutilon theophrasti*); common sunflower (*Helianthus annuus*); ivyleaf morningglory (*Ipomoea hederacea*); common purslane (*Portulaca oleracea*); and common cockleburr (*Xanthium strumarium*). The average control achieved against these broadleaf species ("AVB") is indicated in Table 5.

The soil surface was sprayed inside an enclosed linear spray table with the nozzle set above the soil line. The spray table was calibrated to deliver the appropriate amount to provide the desired application rates, as indicated. After treatment, the flats were placed into a greenhouse and watered as needed. The greenhouse environmental systems provided the plants with natural and artificial lighting to attain 14 hours of light per day. Day and night temperatures were maintained at 29° and 21° C., respectively.

The degree of weed control was evaluated and recorded 17–21 days after treatment as a percentage of weed control as compared to the growth of the same species of the same age in an untreated control flat. Percent control is the total injury to the plants due to all factors including: inhibited emergence, stunting, malformation, chlorosis and other types of plant injury. The control ratings range from 0 to 100 percent, where 0 represents no effect with growth equal to the untreated control and where 100 represents complete kill.

TABLE 5

| Formulation | pH | Application Rate (g/ha) | | Weed Control | |
|---|---|---|---|---|---|
| | | Acetochlor | NMSBC | AVB | AVG |
| Acetochlor/NMSBC-$Cu^{+2}$ | 3 | 30 | 3 | 23 | 66 |
| | | 100 | 10 | 55 | 95 |
| | | 300 | 30 | 85 | 98 |
| | | 900 | 90 | 98 | 100 |
| Acetochlor/NMSBC-$Cu^{+2}$ | 5 | 30 | 3 | 6 | 55 |
| | | 100 | 10 | 32 | 76 |
| | | 300 | 30 | 89 | 100 |
| | | 900 | 90 | 97 | 100 |
| Acetochlor/NMSBC-$Ca^{+2}$ | 7 | 30 | 3 | 2 | 58 |
| | | 100 | 10 | 28 | 92 |
| | | 300 | 30 | 81 | 100 |
| | | 900 | 90 | 97 | 100 |
| Acetochlor/NMSBC-$Co^{+2}$ | 5 | 30 | 3 | 0 | 19 |
| | | 100 | 10 | 18 | 45 |
| | | 300 | 30 | 79 | 87 |
| | | 900 | 90 | 97 | 98 |
| Acetochlor/NMSBC-$Zn^{+2}$ | 5 | 30 | 3 | 4 | 68 |
| | | 100 | 10 | 34 | 95 |
| | | 300 | 30 | 81 | 99 |
| | | 900 | 90 | 97 | 100 |
| Acetochlor/NMSBC-$Fe^{+3}$ | 2 | 30 | 3 | 0 | 19 |
| | | 100 | 10 | 28 | 50 |
| | | 300 | 30 | 77 | 83 |
| | | 900 | 90 | 95 | 97 |
| Acetochlor/NMSBC | — | 30 | 3 | 7 | 69 |
| | | 100 | 10 | 42 | 89 |
| | | 300 | 30 | 95 | 99 |
| | | 900 | 90 | 89 | 100 |

The results shown in Table 5 demonstrate that chelation of NMSBC with transition metal ions does not reduce the herbicidal efficacy of a formulation containing acetochlor and the metal chelate as compared to a similar composition containing acetochlor and non-chelated NMSBC.

EXAMPLE 6

This is an example of a process for preparing a chemically stable, dry form of an herbicidal formulation containing the copper chelate of NMSBC and acetochlor.

The copper chelate of NMSBC was formed in the aqueous phase of a formulation of microencapsulated acetochlor as described in Examples 1 and 3. After formation of the copper chelate, the formulation was spray-dried to remove the water and form a dry formulation. Dry samples were stored at 50° C. and after 2 weeks and then 4 weeks, samples were extracted and analyzed by HPLC, as described previously, to determine the amount of NMSBC remaining. For comparison purposes, a formulation containing unchelated NMSBC in the aqueous phase was also prepared, spray-dried and tested for chemical stability. The results of these tests are shown in Table 6 below.

TABLE 6

| Metal Ion | NMSBC/Metal Molar Ratio | Weight % of NMSBC remaining after storage at 50° C. | |
|---|---|---|---|
| | | 2 weeks | 4 weeks |
| None | N/A | 20.6% | 0.0% |
| $Cu^{+2}$ | 2/1 | 84.4% | 65.2% |
| $Cu^{+2}$ | 2/5 | 98.4% | 101.4% |

The results in Table 6 show that the $Cu^{+2}$ chelate of NMSBC is stable in dry form in the presence of acetochlor microcapsules.

EXAMPLE 7

This is an example of another process for preparing an herbicidal formulation containing the copper chelate of NMSBC and microencapsulated acetochlor in the aqueous phase thereof. Technical grade NMSBC, which had not been milled, was dispersed in the aqueous phase of an herbicidal formulation containing microencapsulated acetochlor. The pH of the formulation was then adjusted to 10 by adding a sufficient amount of sodium hydroxide. An aqueous copper sulfate solution was then added to the formulation while stirring. Instantly, crystals of the copper-NMSBC chelate formed and began to precipitate. The chelation reaction was completed within about 10 minutes. This process was repeated several times to produce mixtures having the NMSBC:$Cu^{+2}$ ratios and pHs shown in Table 7. Samples were stored at 50° C. and extracted and analyzed as described in Example 1, after 4 weeks and 8 weeks storage. The results of this stability testing are shown in Table 7.

TABLE 7

| NMSBC/$Cu^{+2}$ | | Weight % of NMSBC remaining after storage at 50° C. | |
|---|---|---|---|
| Molar Ratio | pH | 4 weeks | 8 weeks |
| 2/1.1 | 5.0 | 97.6% | 95.5% |
| 2/1.1 | 7.0 | 93.2% | 91.1% |

TABLE 7-continued

| NMSBC/$Cu^{+2}$ | | Weight % of NMSBC remaining after storage at 50° C. | |
|---|---|---|---|
| Molar Ratio | pH | 4 weeks | 8 weeks |
| 2/1.5 | 5.0 | 98.1% | n.d. |
| 2/1.5 | 7.0 | 96.9% | n.d. | n.d.—not determined

EXAMPLE 8

Copper chelates of 2-(2'-chloro4'-methylsulfonylbenzoyl)-1,3-cyclohexanedione ("CMSBC"), 2-(2'-nitro-4'-trifluoromethylbenzoyl)-1,3-cyclohexanedione ("NTMBC") and 2-(2'-methyl-4'-methylsulfonylbenzoyl)-4,4,6-trimethyl-1,3-cyclohexanedione ("MMSBTC") were prepared as follows. An aqueous suspension of each cyclohexanedione compound was prepared. An aqueous cupric sulfate solution was added to the cyclohexanedione suspension and the chelation reaction was allowed to proceed to completion. Each copper-chelated cyclohexanedione suspension was then blended with an aqueous formulation of microencapsulated acetochlor which had a pH of about 10. The weight ratio of cyclohexanedione (based on the unchelated cyclohexanedione) to acetochlor in each formulation was 1:10. The pH of the final formulation was adjusted to 5.0 by adding hydrochloric acid.

To test the chemical stability of these cyclohexanedione compounds in an aqueous acetochlor microcapsule formulation, samples of the three formulations prepared above were stored at 50° C. for four weeks. Corresponding samples of the same cyclohexanediones without chelation were also prepared and tested for chemical stability during storage. After storage, samples of both the chelated and unchelated formulations were extracted and analyzed by HPLC, as previously described, to determine the amounts of cyclohexanedione remaining in the formulation. Table 8 shows the results of these storage tests.

TABLE 8

| Compound | Metal Ion | Weight % of Compound remaining after 4 week storage |
|---|---|---|
| CMSBC | $Cu^{+2}$ | 100.0% |
| CMSBC | None | 87.5% |
| NTMBC | $Cu^{+2}$ | 84.5% |
| NTMBC | None | 71.2% |
| MMSBTC | $Cu^{+2}$ | 100.0% |
| MMSBTC | None | 86.2% |

The results shown in Table 8 demonstrate the improved chemical stability exhibited by the $Cu^{+2}$ chelates of a variety of dione compounds as compared to the respective non-chelated compounds.

EXAMPLE 9

This example demonstrates the chemical stability of a copper chelate of NMSBC in an herbicidal formulation of liquid, non-encapsulated acetochlor. An aqueous dispersion of the copper chelate of NMSBC was produced and then this copper chelate was air dried. The dried copper chelate of NMSBC was added to a liquid acetochlor composition which contained dichlormid, a safener for the acetochlor, at an acetochlor:dichlormid ratio of 6:1. The chemical stability of the NMSBC copper chelate in the acetochlor formulation after two weeks storage at 50° C. was determined, using the procedures described in Example 1. The results are shown in Table 9 below, together with the results of a control sample in which the NMSBC was not chelated.

TABLE 9

| Metal Ion | Weight % of NMSBC remaining after 2 week storage |
|---|---|
| $Cu^{+2}$ | 96.3% |
| None | 34.7% |

These results demonstrate the chemical stability of the $Cu^{+2}$ chelate of NMSBC in a non-aqueous liquid herbicidal formulation containing a safener and various formulation additives, such as would be found in many typical commercial formulations of liquid herbicides.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. A chemically stable herbicidal composition comprising, in a liquid medium, a di- or trivalent transition metal chelate of an herbicidal dione of the formula (I):

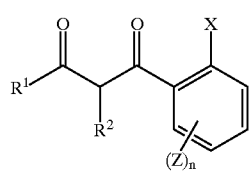

(I)

wherein $R^1$ represents a straight- or branched-chain alkyl, alkenyl or alkynyl group containing up to six carbon atoms which is optionally substituted by one or more halogen atoms; a cycloalkyl group containing from three to six carbon atoms optionally substituted by one or more $R^3$ groups or one or more groups selected from halogen, $—CO_2R^4$; $—SR^5$ and $—OR^5$; a cycloalkenyl group containing five or six carbon atoms optionally substituted by one or more $R^3$ groups or one or more halogen atoms or a group $—CO_2R^4$ or a group of the formula $—(CH_2)_p$-phenyl-$(R^6)_q$;

$R^2$ represents cyano; $—COR^7$; $—CO_2R^7$; or $—S(O)_mR^8$; or $R^1$ and $R^2$ together with the carbon atoms to which they are attached form a five- or six-membered 1,3-cycloalkanedione group, which 1,3-cycloalkanedione group is optionally substituted with from one to six substituents independently selected from halogen, $(C_1–C_6)$alkyl, $(C_1–C_6)$alkoxy, $(C_1–C_6)$haloalkyl, $(C_3–C_6)$cycloalkyl, cyano, nitro, $(C_1–C_6)$ haloalkoxy, $—CO_2R^9$, $—S(O)_mR^{10}$, $—NR^{11}R^{12}$, $—C(O)R^{13}$, $—SO_2NR^{11}R^{12}$, phenyl and phenyl substituted with one or more halo or $C_1–C_4$ alkyl groups, wherein two substituents on the same carbon atom of the 1,3-cycloalkanedione group taken together can form an alkylene group having 2 to 6 carbon atoms;

$R^3$ represents a straight-or branched chain alkyl, alkenyl or alkynyl group containing up to six carbon atoms optionally substituted by one or more halogen atoms; or a cycloalkyl group containing from three to six carbon atoms;

$R^4$ represents a straight- or branched-chain alkyl group containing up to six carbon atoms optionally substituted by one or more halogen atoms; or a cycloalkyl group containing from three to six carbon atoms;

$R^5$ represents a straight- or branched-chain alkyl group containing up to three carbon atoms;

$R^6$ represents a halogen atom or a group selected from $—R^4$, nitro, cyano, $—CO_2R^4$, $—NR^{61}R^{62}$ and $—OR^4$;

$R^{61}$ represents hydrogen, a straight- or branched-chain alkyl group containing up to six carbon atoms optionally substituted by one or more halogen atoms, or a cycloalkyl group containing from three to six carbon atoms;

$R^{62}$ represents a straight- or branched-chain alkyl group containing up to six carbon atoms optionally substituted by one or more halogen atoms, a cycloalkyl group containing from three to six carbon atoms, or a group selected from $—COR^4$, $—CO_2R^4$ and $—CONR^4R^{61}$; wherein $R^4$ and $R^{61}$ are part of a group $—CONR^4R^{61}$ they may, together with the nitrogen to which they are attached, form a five- or six-membered ring optionally having one additional heteroatom in the ring which is oxygen or nitrogen, wherein the ring is optionally substituted by one or more alkyl groups containing up to three carbon atoms; and when $R^{61}$ and $R^{62}$ are part of a group $—NR^{61}R^{62}$ they may, together with the nitrogen to which they are attached, form a five- or six-membered ring optionally having one additional heteroatom in the ring which is oxygen or nitrogen, wherein the ring is optionally substituted by one or more alkyl groups containing up to three carbon atoms;

$R^7$ represents hydrogen or straight- or branched-chain alkyl group containing up to six carbon atoms;

$R^8$ represents $(C_1–C_6)$alkyl, $(C_1–C_6)$haloalkyl, $(C_1–C_6)$ cyanoalkyl $(C_3–C_8)$cycloalkyl optionally substituted with halogen, cyano or $(C_1–C_4)$alkyl; or phenyl optionally substituted with one to three of the same or different halogen, nitro, cyano, $(C_1–C_4)$haloalkyl, $(C_1–C_4$ alkyl, $(C_1–C_4)$alkoxy or $—S(O)_mR^8$;

$R^9$ represents $(C_1–C_4)$alkyl;

$R^{10}$ represents $(C_1–C_4)$alkyl, $(C_1–C_4)$alkyl substituted with halogen or cyano, phenyl or benzyl;

$R^{11}$ and $R^{12}$ independently represents hydrogen or $(C_1–C_4)$alkoxy;

$R^{13}$ represents $(C_1–C_4)$alkyl or $(C_1–C_4)$alkoxy;

X represents a halogen atom; a straight- or branched-chain alkyl or alkoxy group containing up to six carbon atoms which is optionally substituted by one or more groups $—OR^{15}$ or one or more halogen atoms; or a group selected from nitro, cyano, $—CO_2R^{16}$, $—S(O)_mR^{15}$, $—O(CH_2)_rOR^{15}$, $—COR^{16}$, $—OSO_2R^{18}$, $—NR^{16}R^{17}$, $—SO_2NR^{16}R^{17}$, $—CONR^{16}R^{17}$ and $—CSNR^{16}R^{17}$;

$R^{15}$ represents a straight- or branched-chain alkyl group containing up to six carbon atoms which is optionally substituted by one or more halogen atoms;

$R^{16}$ and $R^{17}$ each independently represents a hydrogen atom; or a straight- or branched-chain alkyl group containing up to six carbon atoms which is optionally substituted by one or more halogen atoms;

R$^{18}$ represents a straight- or branched-chain alkyl, alkenyl or alkynyl group containing up to six carbon atoms optionally substituted by one or more halogen atoms; or a cycloalkyl group containing from three to six carbon atoms;

each Z independently represents halo, nitro, cyano, S(O)$_m$R$^2$, OS(O)$_m$R$^2$, (C$_1$–C$_6$)alkyl, (C$_1$–C$_6$)alkoxy, (C$_1$–C$_6$)haloalkyl, (C$_1$–C$_6$)haloalkoxy, carboxy, (C$_1$–C$_6$)alkylcarbonyloxy, (C$_1$–C$_6$)alkoxycarbonyl, (C$_1$–C$_6$)alkylcarbonyl, amino, (C$_1$–C$_6$)alkylamino, (C$_1$–C$_6$)dialkylamino having independently the stated number of carbon atoms in each alkyl group, (C$_1$–C$_6$)alkylcarbonylamino, (C$_1$–C$_6$)alkoxycarbonylamino, (C$_1$–C$_6$)alkylaminocarbonylamino, (C$_1$–C$_6$)dialkylaminocarbonylamino having independently the stated number of carbon atoms in each alkyl group, (C$_1$–C$_6$)alkoxycarbonyloxy, (C$_1$–C$_6$)alkylaminocarbonyloxy, (C$_1$–C$_6$)dialkylaminocarbonyloxy, phenylcarbonyl, substituted phenylcarbonyl, phenylcarbonyloxy, substituted phenylcarbonyloxy, phenylcarbonylamino, substituted phenylcarbonylamino, phenoxy or substituted phenoxy;

m is zero, one or two;

n is zero or an integer from one to four;

p is zero or one;

q is zero or an integer from one to five; and r is one, two or three.

2. A chemically stable herbicidal composition according to claim 1, wherein said liquid medium is a member selected from the group consisting of water, organic solvents and liquid herbicides.

3. A chemically stable herbicidal composition according to claim 1, wherein the transition metal is selected from the group consisting of Cu$^{+2}$, Co$^{+2}$, Zn$^{+2}$ and Ni$^{+2}$.

4. A chemically stable herbicidal composition according to claim 1 having a pH of between about 2 and about 7.

5. A chemically stable herbicidal composition according to claim 1, wherein the molar ratio of the compound of formula (I) to the transition metal is between about 2:1 and 2:5.

6. A chemically stable herbicidal composition according to claim 1, further comprising at least one co-herbicide.

7. A chemically stable herbicidal composition according to claim 6, wherein said co-herbicide is selected from the group consisting of acetanilides, tralkoxydim, bromoxynil and its esters, thiafluamide, MCPA and its esters, 2,4-D and its esters, and fluroxypyr meptyl.

8. A chemically stable herbicidal composition according to claim 6, wherein said liquid medium is a co-herbicide.

9. A chemically stable herbicidal composition according to claim 6, wherein said liquid medium is water.

10. A chemically stable herbicidal composition according to claim 6, wherein said liquid medium comprises a microencapsulated co-herbicide dispersed in water.

11. A chemically stable herbicidal composition according to claim 1, wherein the herbicidal dione is of the formula:

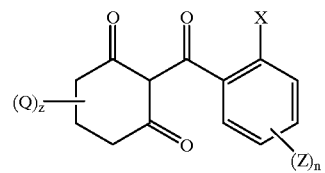

wherein X, Z and n have the same meanings as in claim 1; each Q independently represents C$_1$–C$_4$ alkyl or —CO$_2$R$^a$ wherein R$^a$ is C$_1$–C$_4$ alkyl; and z is 0 or an integer from 1 to 6.

12. A chemically stable herbicidal composition according to claim 11, wherein z is zero; X is chloro, bromo, nitro, cyano, C$_1$–C$_4$ alkyl, —CF$_3$, —S(O)$_m$R$^{15}$ or —OR$^{15}$; and n is one or two; and each Z is independently chloro, bromo, nitro, cyano, C$_1$–C$_4$ alkyl, —CF$_3$, —OR$^{15}$, —OS(O)$_m$R$^2$ or —S(O)$_m$R$^2$.

13. A chemically stable herbicidal composition according to claim 11, wherein the herbicidal dione is a member selected from the group consisting of 2-(2'-nitro-4'-methylsulfonylbenzoyl)-1,3-cyclohexanedione, 2-(2'-nitro-4'-methylsulfonyloxybenzoyl)-1,3-cyclohexanedione and 2-(2'-chloro-4'-methylsulfonylbenzoyl)-1,3-cyclohexanedione.

14. A chemically stable herbicidal composition according to claim 1, wherein the herbicidal dione is of the formula:

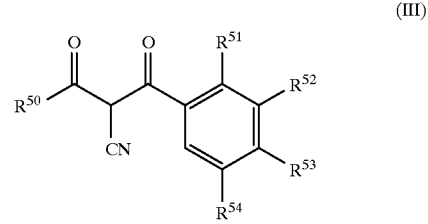

wherein:

R$^{50}$ is a straight- or branched-chain alkyl group containing up to six carbon atoms which is optionally substituted by one or more halogen atoms which may be the same or different; or a cycloalkyl group containing from three to six carbon atoms which is optionally substituted by one or more groups selected from R$^{55}$ and one or more halogen atoms which may be the same or different;

one of R$^{51}$ and R$^{53}$ is —S(O)$_t$R$^{56}$ and the other of R$^{51}$ and R$^{53}$ is a halogen atom; a straight- or branched-chain alkyl group containing up to six carbon atoms which is substituted by —OR$^{55}$; —R$^{55}$; nitro; cyano; —SR$^{55}$; —OR$^{55}$; —O(CH$_2$)$_s$OR$^{55}$; or —CO$_2$R$^{55}$; and when R$^{51}$ is —S(O)$_t$R$^{56}$, R$^{53}$ may be hydrogen;

R$^{52}$ and R$^{54}$, which may be the same or different, each is a halogen atom; a hydrogen atom; a straight- or branched-chain alkyl group containing up to six carbon atoms which is substituted by —OR$^{55}$; —R$^{55}$; nitro; cyano; —OR$^{55}$; —O(CH$_2$)$_s$OR$^{55}$; or —CO$_2$R$^{55}$;

R$^{55}$ and R$^{56}$, which may be the same or different, each is a straight- or branched-chain alkyl group containing up to six carbon atoms which is optionally substituted by one or more halogen atoms which may be the same or different;

s is an integer from 1 to 3; and t is zero, 1 or 2.

15. A chemically stable herbicidal composition according to claim 14, wherein $R^{50}$ is a cycloalkyl group.

16. A chemically stable herbicidal composition according to claim 14, wherein the herbicidal dione is a member selected from the group consisting of 2-cyano-1-[2-chloro-3-ethoxy-4-(ethylsulfonyl)phenyl]-3-cyclopropylpropan-1,3-dione; 2-cyano-1-[4-chloro-2-(methylsulfonyl)phenyl]-3-cyclopropylpropan-1,3-dione; 2-cyano-1-[2-methylsulfonyl-4-(trifluoromethyl)phenyl]-3-cyclopropylpropan-1,3-dione; and 2-cyano-1-[4-bromo-2-(methylsulfonyl)phenyl]-3-cyclopropylpropan-1,3-dione.

17. A dry, chemically stable herbicidal composition comprising a di- or trivalent transition metal chelate of an herbicidal dione of the formula (I):

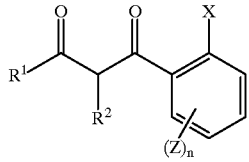

(I)

wherein
$R^1$ represents a straight- or branched-chain alkyl, alkenyl or alkynyl group containing up to six carbon atoms which is optionally substituted by one or more halogen atoms; a cycloalkyl group containing from three to six carbon atoms optionally substituted by one or more $R^3$ groups or one or more groups selected from halogen, $-CO_2R^4$; $-SR^5$ and $-OR^5$; a cycloalkenyl group containing five or six carbon atoms optionally substituted by one or more $R^3$ groups or one or more halogen atoms or a group $-CO_2R^4$ or a group of the formula $-(CH_2)_p$-phenyl-$(R^6)_q$;

$R^2$ represents cyano; $-COR^7$; $-CO_2R^7$; or $-S(O)_mR^8$; or $R^1$ and $R^2$ together with the carbon atoms to which they are attached form a five- or six-membered 1,3-cycloalkanedione group, which 1,3-cycloalkanedione group is optionally substituted with from one to six substituents independently selected from halogen, $(C_1-C_6)$alkyl, $(C_1-C_6)$alkoxy, $(C_1-C_6)$haloalkyl, $(C_3-C_6)$cycloalkyl, cyano, nitro, $(C_1-C_6)$haloalkoxy, $-CO_2R^9$, $-S(O)_mR^{10}$, $-NR^{11}R^{12}$, $-C(O)R^{13}$, $-SO_2NR^{11}R^{12}$, phenyl and phenyl substituted with one or more halo or $C_1-C_4$ alkyl groups, wherein two substituents on the same carbon atom of the 1,3-cycloalkanedione group taken together can form an alkylene group having 2 to 6 carbon atoms;

$R^3$ represents a straight- or branched chain alkyl, alkenyl or alkynyl group containing up to six carbon atoms optionally substituted by one or more halogen atoms; or a cycloalkyl group containing from three to six carbon atoms;

$R^4$ represents a straight- or branched-chain alkyl group containing up to six carbon atoms optionally substituted by one or more halogen atoms; or a cycloalkyl group containing from three to six carbon atoms;

$R^5$ represents a straight- or branched-chain alkyl group containing up to three carbon atoms;

$R^6$ represents a halogen atom or a group selected from $-R^4$, nitro, cyano, $-CO_2R^4$, $-NR^{61}R^{62}$ and $-OR^4$;

$R^{61}$ represents hydrogen, a straight- or branched-chain alkyl group containing up to six carbon atoms optionally substituted by one or more halogen atoms, or a cycloalkyl group containing from three to six carbon atoms;

$R^{62}$ represents a straight- or branched-chain alkyl group containing up to six carbon atoms optionally substituted by one or more halogen atoms, a cycloalkyl group containing from three to six carbon atoms, or a group selected from $-COR^4$, $-CO_2R^4$ and $-CONR^4R^{61}$; wherein $R^4$ and $R^{61}$ are part of a group $-CONR^4R^{61}$ they may, together with the nitrogen to which they are attached, form a five- or six-membered ring optionally having one additional heteroatom in the ring which is oxygen or nitrogen, wherein the ring is optionally substituted by one or more alkyl groups containing up to three carbon atoms; and when $R^{61}$ and $R^{62}$ are part of a group $-NR^{61}R^{62}$ they may, together with the nitrogen to which they are attached, form a five- or six-membered ring optionally having one additional heteroatom in the ring which is oxygen or nitrogen, wherein the ring is optionally substituted by one or more alkyl groups containing up to three carbon atoms;

$R^7$ represents hydrogen or straight- or branched-chain alkyl group containing up to six carbon atoms;

$R^8$ represents $(C_1-C_6)$alkyl, $(C_1-C_6)$haloalkyl, $(C_1-C_6)$cyanoalkyl $(C_3-C_8)$cycloalkyl optionally substituted with halogen, cyano or $(C_1-C_4)$alkyl; or phenyl optionally substituted with one to three of the same or different halogen, nitro, cyano, $(C_1-C_4)$haloalkyl, $(C_1-C_4$ alkyl, $(C_1-C_4)$alkoxy or $-S(O)_mR^8$;

$R^9$ represents $(C_1-C_4)$alkyl;

$R^{10}$ represents $(C_1-C_4)$alkyl, $(C_1-C_4)$alkyl substituted with halogen or cyano, phenyl or benzyl;

$R^{11}$ and $R^{12}$ independently represents hydrogen or $(C_1-C_4)$alkoxy;

$R^{13}$ represents $(C_1-C_4)$alkyl or $(C_1-C_4)$alkoxy;

X represents a halogen atom; a straight- or branched-chain alkyl or alkoxy group containing up to six carbon atoms which is optionally substituted by one or more groups $-OR^{15}$ or one or more halogen atoms; or a group selected from nitro, cyano, $-CO_2R^{16}$, $-S(O)_mR^{15}$, $-O(CH_2)_rOR^{15}$, $-COR^{16}$, $-OSO_2R^{18}$, $-NR^{16}R^{17}$, $-SO_2NR^{16}R^{17}$, $-CONR^{16}R^{17}$ and $-CSNR^{16}R^{17}$;

$R^{15}$ represents a straight- or branched-chain alkyl group containing up to six carbon atoms which is optionally substituted by one or more halogen atoms;

$R^{16}$ and $R^{17}$ each independently represents a hydrogen atom; or a straight- or branched-chain alkyl group containing up to six carbon atoms which is optionally substituted by one or more halogen atoms;

$R^{18}$ represents a straight- or branched-chain alkyl, alkenyl or alkynyl group containing up to six carbon atoms optionally substituted by one or more halogen atoms; or a cycloalkyl group containing from three to six carbon atoms;

each Z independently represents halo, nitro, cyano, $S(O)_mR^2$, $OS(O)_mR^2$, $(C_1-C_6)$alkyl, $(C_1-C_6)$alkoxy, $(C_1-C_6)$haloalkyl, $(C_1-C_6)$haloalkoxy, carboxy, $(C_1-C_6)$alkylcarbonyloxy, $(C_1-C_6)$alkoxycarbonyl, $(C_1-C_6)$alkylcarbonyl, amino, $(C_1-C_6)$alkylamino, $(C_1-C_6)$dialkylamino having independently the stated number of carbon atoms in each alkyl group, $(C_1-C_6)$alkylcarbonylamino, $(C_1-C_6)$alkoxycarbonylamino, $(C_1-C_6)$alkylaminocarbonylamino, $(C_1-C_6)$dialkylaminocarbonylamino having independently the stated number of carbon atoms in each alkyl group, $(C_1-C_6)$alkoxycarbonyloxy, $(C_1-C_6)$alkylaminocarbonyloxy, $(C_1-C_6)$dialkylaminocarbonyloxy, phenylcarbonyl, substituted phenylcarbonyl, phenylcarbonyloxy, substituted phenylcarbonyloxy, phenylcarbonylamino, substituted phenylcarbonylamino, phenoxy or substituted phenoxy;

m is zero, one or two;

n is zero or an integer from one to four;

p is zero or one;

q is zero or an integer from one to five; and r is one, two or three.

18. A dry, chemically stable herbicidal composition according to claim 17, further comprising at least one co-herbicide.

19. A dry, chemically stable herbicidal composition according to claim 18, wherein said co-herbicide is selected from the group consisting of acetanilides, tralkoxydim, bromoxynil and its esters, thiafluamide, MCPA and its esters, 2,4-D and its esters, and fluroxypyr meptyl.

20. A process for producing a chemically stable composition of claim 1, comprising the steps of:

adding an herbicidal dione of formula (I) to a liquid medium to produce a first mixture;

adding an aqueous solution of a di- or trivalent transition metal salt to said first mixture, said metal salt solution being added in an amount sufficient to provide a stoichiometric excess of said metal relative to said herbicidal dione;

allowing said metal salt and said herbicidal dione to react for a period of time sufficient to convert all of said herbicidal dione to its corresponding metal chelate; and then adjusting the pH of the resulting composition to between about 2 and 7.

21. A process according to claim 20, wherein said liquid medium is water.

22. A process according to claim 21, wherein said liquid medium comprises a microencapsulated herbicide dispersed in water.

23. A process according to claim 20, wherein said herbicidal dione is solid and said process comprises the steps of:

milling said herbicidal dione;

adding an herbicidal dione of formula (I) to a liquid medium to produce a first mixture;

adding an aqueous solution of a di- or trivalent transition metal salt to said first mixture, said metal salt solution being added in an amount sufficient to provide a stoichiometric excess of said metal relative to said herbicidal dione;

allowing said metal salt and said herbicidal dione to react for a period of time sufficient to convert all of said herbicidal dione to its corresponding metal chelate; and then adjusting the pH of the resulting composition to between about 2 and 7.

24. A process according to claim 20, wherein said process comprises the steps of:

adding an herbicidal dione of formula (I) to a liquid medium to produce a first mixture;

adjusting the pH of said first mixture to about 10; and then adding an aqueous solution of a di- or trivalent transition metal salt to said first mixture, said metal salt solution being added in an amount sufficient to provide a stoichiometric excess of said metal relative to said herbicidal dione;

allowing said metal salt and said herbicidal dione to react for a period of time sufficient to convert all of said herbicidal dione to its corresponding metal chelate; and then adjusting the pH of the resulting composition to between about 2 and 7.

* * * * *